(12) United States Patent
De Ambrosi et al.

(10) Patent No.: US 7,605,242 B2
(45) Date of Patent: *Oct. 20, 2009

(54) PROCESS FOR THE PHYSICAL DEPOLYMERIZATION OF GLYCOSAMINOGLYCANES AND PRODUCTS OBTAINED THEREFROM

(75) Inventors: Luigi De Ambrosi, Santhià (IT); Donata Bensi, Vercelli (IT); Elena Vismara, Milan (IT)

(73) Assignee: Laboratori Derivati Organici S.p.A., Vercelli (VC) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 10/555,897

(22) PCT Filed: May 6, 2004

(86) PCT No.: PCT/EP2004/050723

§ 371 (c)(1),
(2), (4) Date: Apr. 18, 2006

(87) PCT Pub. No.: WO2004/099256

PCT Pub. Date: Nov. 18, 2004

(65) Prior Publication Data

US 2006/0237302 A1    Oct. 26, 2006

(30) Foreign Application Priority Data

May 9, 2003    (EP)    .................... 03076388

(51) Int. Cl.
C08B 37/00    (2006.01)
C08B 37/10    (2006.01)
(52) U.S. Cl. .............................. 536/21; 536/53; 536/54; 204/157.68
(58) Field of Classification Search .................. 536/21, 536/53, 54; 204/157.68
See application file for complete search history.

(56) References Cited

U.S. PATENT DOCUMENTS 7,091,337 B2 *  8/2006  De Ambrosi et al. ........ 536/124

FOREIGN PATENT DOCUMENTS

KR    2000012173 A    5/2000
WO    WO 90/04607 A2    5/1990

OTHER PUBLICATIONS

Balazs et al., *Radiation Research*, 11:149-164 (1959).
Blažková et al., *Journal of Materials Science*, 30:729-733 (1995).
Khan et al., *Polymer Photochemistry*, 6:465-474 (1985).

* cited by examiner

*Primary Examiner*—Shaojia Anna Jiang
*Assistant Examiner*—Ganapathy Krishnan
(74) *Attorney, Agent, or Firm*—Katten Muchin Rosenman LLP; Justin L. Krieger

(57) ABSTRACT

The invention relates to a process for the depolymerization of glycosaminoglycanes characterized by the use of UVC radiation. The invention also relates to the intermediate depolymerized heparin obtained by the process. The intermediate depolymerized heparin can be dissolved in a buffer solution and fractionated by gel permeation for obtaining the desired molecular weight.

7 Claims, No Drawings

PROCESS FOR THE PHYSICAL DEPOLYMERIZATION OF GLYCOSAMINOGLYCANES AND PRODUCTS OBTAINED THEREFROM

This application is a United States national filing under 35 U.S.C. §371 of international (PCT) application No. PCT/EP04/050723, filed May 6, 2004, designating the US and claiming priority to European Application No. 03076388.0, filed May 9, 2003.

STATE OF THE ART

Glycosaminoglycanes are natural products of large pharmaceutical interest. Among the most widely used we can mention heparin, dermatan, heparansulphate and chondroitines.

The molecular weight of the natural products varies considerably and normally ranges from 5 to 40 kDa. It is however known that, for certain applications, lower molecular weights lead to higher pharmacological activity. The high molecular weight of these compounds often renders impossible their oral administration. Furthermore, it is known that specific activities of glycosaminoglycanes are related to relatively short saccharide sequences. Thus, it would be very advantageous to depolymerize glycosaminoglycanes reducing the molecular weight without loosing the active sites present in the molecule. The chemical depolymerization of glycosaminoglycanes is well known in the art and leads to glycosaminoglycanes of lower MW but also with a lower S content.

EP 394 971 discloses an enzymatic or chemical depolymerization process. The obtained heparin oligomers have a sulphur content lower than 9%.

WO 90/04607 discloses a depolymerization of heparin and dermatansulfate by the use of $H_2O_2$ and $Cu^{2+}$. The ratio $SO_3^-/COO^-$ is slightly lower than in the starting heparin.

U.S. Pat. No. 4,987,222 discloses a method for the depolymerization of heparin by the use of gamma rays. The examples disclose the preparation of heparin of Mw around 5,000 Da and with a high S content. However, the heparin produced by this method presents a certain amount of degradation products as a result of uncontrolled side reactions.

It is therefore desirable to reduce the molecular weight of glycosaminoglycanes without substantially modifying the chemical structure of the same.

It is know in the art that the irradiation of glycosaminoglycanes with UV leads to their degradation. For example, in Polymer Photochemistry 6 (1985) 465-474, Khan et al. studied the effect of UV radiation on aqueous solution of heparin-Ca salts. Depolymerization was detected, but it was only considered as a degradation process, not as a potential industrial process for the controlled depolymerization of heparin.

SUMMARY OF THE INVENTION

The present invention relates to a physical process for the depolymerization of glycosaminoglycanes by the use of WNC radiation having a peak in the range from 245 nm to 260 nm. It also relates to the glycosaminoglycanes obtained by this process.

DETAILED DESCRIPTION OF THE INVENTION

The present invention provides a physical depolymerization process which reduces the molecular weight of glycosaminoglycanes without substantially modifying the chemical structure of the same.

The objective is achieved through use of INC radiation. When using heparin as a starting material, this process results in a low to ultra-low molecular weight heparin characterized by high S content.

The starting materials to be used in the process according to the present invention are natural glycosaminoglycanes such as heparin, heparansulphate, dermatane and chondroitine. Other suitable starting materials are derivatives of glycosaminoglycanes obtained by known methods. Thus, for example, the N-acetyl or N-sulphate groups of the residues of hexosamine can be transformed in amino groups through N-desulphation or N-deacetylation reactions and the sulphate groups of the uronic acids through desulphation reactions can give rise to epoxy groups.

In another embodiment, it is possible to use as a starting material for the process of the present invention a glycosaminoglycane which has already undergone a depolymnerization process either chemical, physical or enzymatic. Examples of physical depolymerization methods that can be used in combination with the process of the invention are described in WO 03/076474 (LDO) and WO 2004/000886 (LDO), which are herewith incorporated by reference. The use of partly depolymerized glycosaminoglycanes is for example relevant in case of heparin which has undergone an acid pretreatment that has as a side effect partial depolymerization, or when depolymerizing functionalized glycosaminoglycanes. The conditions used for the introduction of functional groups are sometimes also causing reduction of the molecular weight of the polysaccharide.

Thus, not only it is possible to perform both steps by using WVC radiation, but it is possible to perform a first depolymerization step by using INC radiation followed by a second step using chemical-enzymatic depolymerization, or to perform a first step of chemical-enzymatic depolymerization followed by UVC radiation depolymerization. The process of the present invention allows reduction of the molecular weight of the glycosaminoglycane without sensible modification of the chemical structure of the polysaccharide. The Mw of the glycosaminoglycane after irradiation is equal to or lower than 50% of the Mw of the glycosaminoglycane prior to irradiation Absorption by a molecule of radiation in the ultraviolet (200-400 nm) or visible (400-800 nm) region of the spectrum can result in an excited state so high in energy that the energy absorbed is comparable in magnitude with the bond dissociation energies associated with organic molecules. If absorption occurs at 250 nm, the energy associated with this transition ($E=480$ kJ $mol^{-1}$) is greater than the bond dissociation energies of a carbon-carbon σ-bond ($D\approx347$ kJ $mol^{-1}$), a carbon-oxygen σ-bond ($D\approx330$ kJ $mol^{-1}$) and a carbon-hydrogen bond ($D\approx414$ kJ $mol^{-1}$), average values in polyatomic molecules. It is not surprising therefore that chemical reaction can be induced by excitation with ultraviolet light. Generally speaking, homolytic cleavages of a covalent bond in organic molecules can be induced by UV radiation, forming two intermediate radicals.

Mercury vapour arc lamps are now the source of choice for most photochemical reactions in solution phase. These sources provide radiation in the ultraviolet and visible parts of the spectrum covering a range from 200 nm to 750 nm and so are useful for practically all purposes. There are three main type of mercury lamps designed as low, medium and high pressure and each has a different characteristic. The low pressure lamp operates at room temperature and mainly emits at 253.27 and 184.9 nm. Medium pressure lamps exhibit a weak continuum with a superimposition of spectral lines, associated with a diminished intensity at 253.27 and 184.9 nm. For the high pressure lamp, the large increase in pressure introduces many more lines. The emission below 280 nm is very weak. 189.4 nm radiation (far UV) is absorbed by the solvent, water. When absorption occurs at 184.9 nm, the energy associated with this transition is E=649 kJ mol$^{-1}$ As the bond dissociation energy of oxygen-hydrogen is ≈455 kJ mol$^{-1}$, average value in polyatomic molecules, this radiation can generate H. and OH. from water. 194.2 nm (far UV) and 253.27 nm are absorbed by the heparin molecule. Above 300 nm, heparin does not absorb.

The present invention relates to the use of UV radiation having an emission peak in the range from 245 nm to 260 nm, preferably from mercury lamps, most preferably low and medium pressure lamps.

In another embodiment the present invention is directed to the use of UV radiation prevalently at the wavelength of about 253 nm. In fact, it is possible to use filters that absorb the radiation at different wavelength and let pass only the 253 nm radiation. In this way it is possible to minimize side reactions as described before and obtain a high selectivity in the depolymerization reaction.

Without limiting the scope of the invention, it is believed that the radiation at 253 nm can produce dissociation of glycosidic bond and this is believed to be an important step in the depolymerisation. The excited molecule releases energy by forming two intermediate radicals, that somehow evolve to stable structures of lower $M_w$.

Although the mechanism of depolymerization is still unclear, we suppose that the formed free-radicals can be trapped by the oxygen present in water, and the resulting oxygen-oxygen bond can be cleaved with a mechanism similar to common autooxidation induced by atmospheric oxygen and sunlight (oxygen-oxygen (σ-bond: D≈137 kJ mol$^{-1}$). We can describe this pathway to depolymerization, C—O—C→C—OH +C—OH, as autooxidation of glycosidic bonds.

However, the process can be performed also in the absence of oxygen, indicating the presence of other mechanisms of evolution of the free-radicals which do not require reaction with oxygen.

The process of the invention is usually performed on a aqueous solution of the glycosaminoglycane.

The concentration of glycosarninoglycane in the solution can vary in a broad range. Preferably it is comprised between 2 and 25% w/v, more preferably between 4 and 15%. The pH of the aqueous solution is preferably kept in the range of 3.0 to 7.0, most preferably between 4.0 and 6.0. In fact, when the solution is basic, anionic depolymerization of the glycosaminoglycane takes place.

To regulate the pH to the desired value, it is possible to use weak acids such as acetic acid, citric acid and the like.

After irradiation, the solutions is very clear and does not require any treatment to remove colored substances.

It is also possible to fractionate the intermediate depolymerized glycosaminoglycane by Gel Permeation Chromatography. The fractions containing the desired molecular weights are collected, concentrated by ultra filtration and lyophilized.

The process of the present invention is preferably performed by using a dynamic irradiation process.

With the term "dynamic irradiation process" it is meant a process wherein the solution to be irradiated is circulating as a thin layer in a lamp jacket and then returns to a reservoir where it is preferably thermostated. The liquid can circulate in one or more lamps which can be connected in series or in parallel.

The flow-rate of the solution in the circuit is not critical, but it is preferred to have a flow-rate high enough to avoid overheating of the solution.

The temperature of the solution in the circuit can vary in a broad range. Preferably it is maintained between 0 and 70° C., more preferably between 10 and 60° C.

The process can be performed either in batch or in continuous mode. The apparatus is preferably formed of a reservoir from which the liquid moves to the irradiation area.

The liquid is then returned to the reservoir.

In another embodiment of the invention, the solution is continuously withdrawn from the reservoir and subjected to membrane filtration with a cut off that can vary according to the desired target of MW.

For example, when willing to obtain depolymerised heparin with a $M_w$ comprised between 2,000 and 3,000, it is possible to use a cut off of 5,000 Da. If the desired $M_w$ is below 2,000 Da, then it is possible to use a cut off of 3,000 Da.

By the use of this continuous membrane filtration step, the solution which undergoes irradiation is maintained at a higher $M_w$. It is therefore possible to avoid formation of very small heparin fragments which present lower pharmaceutical activity.

EXPERIMENTAL SECTION

Molecular mass (Mw) was determined by size exclusion chromatography (European Pharmacopoeia 4$^{th}$ ed.: 2.2.30 and 2.2.46 for chromatography techniques and 01/2002:0828 p. 1297 for method).

Absorbance at 260 nm was determined according to European Pharmacopoeia 4$^{th}$ ed 01/2002:0828 p. 1297.

Anti Xa activity was determined according to the method described in European Pharmacopoeia 4$^{th}$ ed.: 2.2.30 and 2.2.46 for chromatography techniques and 01/2002:0828 p. 1297 for method.

Anti coagulant activity was determined according to the method described in European Pharmacopoeia 4$^{th}$ ed.: 2.7.5 pg 168.

EXAMPLE 1

5l of a 10% solution of heparin Na salt having Mw 13.000 Da, are introduced into the irradiation system formed of a reservoir, a circuit of 4 lamps (total W460), a peristaltic pump circulating the liquid into the circuit (19 l/h), and a small heat exchanger refrigerating the solution to 30° C.

The liquid is irradiated for 16 hours.

Heparin is collected, spray-dried and analysed.

Mw=5.000

Absorbance at 260 nm (solution 0.4%)=0.080

Inorganic sulphates=absent aXa activity=106 U/mg

Anticoagulant activity=114 U/mg

NMR: values obtained by intregation of $^{13}$C-NMR signals

| | Sample | | | | | | | |
|---|---|---|---|---|---|---|---|---|
| | $A_{NS6X}$-G | $A_{NS6X}$-$I_{2X}$ | $A_{NAc}$ | $A_{N,3,6S}$ | $A_{6S}$ | $I_{2S}$ | $I_{2OH}$ | G |
| Starting heparin | 12.92 | 68.08 | 13.6 | 4.6 | 75.9 | 61.4 | 13.26 | 25.7 |
| Depolym. heparin | 13.6 | 64.18 | 15.8 | 6.4 | 77.9 | 60.8 | 17.2 | 22 |

The obtained intermediate depolymerised heparin can be fractionated by Gel Permeation Chromatography. The fractions containing the desired molecular weights are collected, concentrated by ultra filtration and lyophilized.

EXAMPLE 2

Example 1 was repeated but continuously filtering the liquid with a membrane having a cut off value of 5.000 Da. The liquid removed by membrane filtration is continuously integrated by addition of starting 10% heparin-Na salt solution.

EXAMPLE 3

Example 1 was repeated but using a 5% dermatan sulphate (Mw=35.000 Da) solution instead of a 10% heparin solution.

After irradiation, the recovered dermatan sulphate had the following characteristics:
Mw=15.000 Da
Abs 260 nm=0.150
Inorganic sulphates=absent The obtained intermediate depolymerised dermatan sulphate can be fractionated by Gel Permeation Chromatography. The fractions containing the desired molecular weights are collected, concentrated by ultra filtration and lyophilized.

EXAMPLE 4

2.5 l of a 10% solution of heparin Na salt having Mw 14.238 Da, were introduced into the irradiation system formed of a reservoir, a circuit containing a 115 W lamp, a peristaltic pump circulating the liquid into the circuit (25 l/h), and a small heat exchanger refrigerating the solution to 30° C.

The solution was irradiated for 36 h and samples were taken to measure the Mw.

EXAMPLE 5

Example 4 was repeated at 56° C.

Table 1 reports the results obtained at 30 and 56° C.

The results show that the increase of temperature from 30 to 56° C. results in a higher depolymerization rate and a slight increase in the absorption at 260 and 280 nm, which remains however very low.

| Time (hours) | Example 4 30° C. | Example 5 56° C. |
|---|---|---|
| 0 | 14238 | 14238 |
| 6 | 12718 | 11418 |
| 12 | 11975 | 10574 |
| 18 | | 9930 |
| 24 | 10629 | 9000 |
| 36 | 9741 | 7829 |

| Analysis | Example 4 | Example 5 |
|---|---|---|
| Abs at 260 nm | 0.044 | 0.074 |
| Abs at 280 nm | 0.039 | 0.068 |

The invention claimed is:

1. A dynamic irradiation process for the depolymerization of heparin wherein the depolymerized heparin has a $M_w$ less than or equal to 50% of the original $M_w$ of said heparin prior to depolymerization, said dynamic irradiation process comprising exposing said heparin in solution at a concentration between 2 and 25% w/v to UV radiation having a peak of from 245 nm to 260 nm for a sufficient time to reduce the $M_w$ of the depolymerized heparin by at least 50% as compared with the $M_w$ of said heparin prior to said exposure to UV radiation.

2. The dynamic irradiation process according to claim 1, wherein the source of UV radiation is a medium or low pressure Hg lamp.

3. The dynamic irradiation process according to claim 1, wherein the UV radiation has a prevalent emission band at 253 nm.

4. The dynamic irradiation process according to any one of claims 1, 2, or 3, wherein the depolymerization process is carried out at a temperature of between 0 and 70° C.

5. The dynamic irradiation process according to any one of claims 1, 2, or 3, wherein the depolymerization process is carried out at a temperature of between 10 and 60° C.

6. The dynamic irradiation process according to any one of claims 1, 2, or 3, wherein the solution has a concentration between 4 and 15% w/v.

7. The dynamic irradiation process according to claim 1, wherein the process allows reduction of molecular weight without modification of the chemical structure of the heparin.

* * * * *